United States Patent
Kakuma

(10) Patent No.: US 10,799,099 B2
(45) Date of Patent: Oct. 13, 2020

(54) OPTICAL INTERFERENCE TOMOGRAPHIC IMAGE GENERATING APPARATUS AND METHOD FOR USING SAME

(71) Applicant: The Yoshida Dental Mfg. Co., Ltd., Tokyo (JP)

(72) Inventor: Hideo Kakuma, Tokyo (JP)

(73) Assignee: The Yoshida Dental Mfg. Co., Ltd., Tokyo (JP)

( * ) Notice: Subject to any disclaimer, the term of this patent is extended or adjusted under 35 U.S.C. 154(b) by 132 days.

(21) Appl. No.: 16/085,657

(22) PCT Filed: Mar. 8, 2017

(86) PCT No.: PCT/JP2017/009343
§ 371 (c)(1),
(2) Date: Sep. 17, 2018

(87) PCT Pub. No.: WO2017/159513
PCT Pub. Date: Sep. 21, 2017

(65) Prior Publication Data
US 2019/0029505 A1  Jan. 31, 2019

(30) Foreign Application Priority Data
Mar. 18, 2016 (JP) .................. 2016-054859

(51) Int. Cl.
*A61B 1/045* (2006.01)
*A61B 1/24* (2006.01)
(Continued)

(52) U.S. Cl.
CPC ............... *A61B 1/045* (2013.01); *A61B 1/00* (2013.01); *A61B 1/00009* (2013.01);
(Continued)

(58) Field of Classification Search
CPC ... G01B 9/02091; A61B 3/102; A61B 5/0066; A61B 5/4547
See application file for complete search history.

(56) References Cited

U.S. PATENT DOCUMENTS 7,702,139 B2 * 4/2010 Liang ................. A61B 1/0638
382/128
8,670,126 B2  3/2014 Kabetani et al.
(Continued)

FOREIGN PATENT DOCUMENTS

CN 102192896 A 9/2011
CN 204636295 U 9/2015
(Continued)

OTHER PUBLICATIONS

Office Action from corresponding CN 201780004972.X dated Aug. 29, 2019, by Chinese National Intellectual Property Administration—Chinese Version (6 pages).
(Continued)

Primary Examiner — Shawn Decenzo
(74) Attorney, Agent, or Firm — Capitol City TechLaw, PLLC; Samuel P. Burkholder

(57) ABSTRACT

Provided are an optical interference tomographic image generating apparatus and a method for using the same, whereby an image can be acquired in which the effect of unnecessary matter near a sample is reduced. An optical interference tomographic image generating apparatus is provided with an OCT control device for performing image processing for vertically inverting an image generated from a detection signal in the case of a setting whereby a reference mirror is disposed so that the optical path length of a reference optical path matches the optical path length of a sample optical path having as a reference position a position at a greater depth along the optical axis of a sample than a subject.

3 Claims, 11 Drawing Sheets

(51) Int. Cl.
    *A61B 3/10*     (2006.01)
    *G01N 21/17*     (2006.01)
    *A61B 1/00*     (2006.01)
    *A61B 5/00*     (2006.01)
    *G01B 9/02*     (2006.01)
    *A61B 1/06*     (2006.01)

(52) U.S. Cl.
    CPC .............. *A61B 1/0669* (2013.01); *A61B 1/24* (2013.01); *A61B 3/10* (2013.01); *A61B 3/102* (2013.01); *A61B 5/0066* (2013.01); *A61B 5/4547* (2013.01); *G01B 9/02091* (2013.01); *G01N 21/17* (2013.01)

(56) References Cited

U.S. PATENT DOCUMENTS

| | | | | |
|---|---|---|---|---|
| 2005/0083536 A1* | 4/2005 | Fouquet | ............... | A61B 5/0066 356/512 |
| 2008/0063998 A1* | 3/2008 | Liang | ................ | A61B 1/0638 433/29 |
| 2010/0014089 A1* | 1/2010 | Yamada | ................. | A61B 3/102 356/450 |
| 2011/0228221 A1* | 9/2011 | Hanebuchi | ............. | A61B 3/102 351/206 |
| 2012/0013722 A1* | 1/2012 | Wong | ................ | A61B 1/00009 348/66 |
| 2012/0281235 A1* | 11/2012 | Murata | .................. | A61B 3/102 356/479 |
| 2013/0242258 A1* | 9/2013 | Higuchi | ............... | A61B 5/0066 351/206 |
| 2014/0009738 A1* | 1/2014 | Satake | ................... | A61B 3/102 351/206 |
| 2014/0192323 A1* | 7/2014 | Kakuma | ............. | A61B 5/0066 351/206 |

FOREIGN PATENT DOCUMENTS

| | | |
|---|---|---|
| JP | 2013-188316 A | 9/2013 |
| JP | 2014-061089 A | 4/2014 |
| JP | 2016-007488 A | 1/2016 |
| WO | 2012140926 A1 | 10/2012 |

OTHER PUBLICATIONS

Office Action from corresponding CN 201780004972.X dated Aug. 29, 2019, by Chinese National Intellectual Property Administration—English Version (5 pages).

International Search Report from PCT/JP2017/009343 dated May 30, 2017, by Japan Patent Office—English Version (2 pages).

International Search Report from PCT/JP2017/009343 dated May 30, 2017, by Japan Patent Office—Japanese Version (2 pages).

Written Opinion of the International Searching Authority from PCT/JP2017/009343 dated May 30, 2017, by International Searching Authority—Japanese (3 pages).

* cited by examiner

OPTICAL INTERFERENCE TOMOGRAPHIC IMAGE GENERATING APPARATUS AND METHOD FOR USING SAME

CROSS-REFERENCE TO RELATED APPLICATION

This application is a U.S. National Stage Application under 35 U.S.C § 371 of International Patent Application No. PCT/JP2017/009343 filed Mar. 8, 2017, which claims the benefit of priority to Japanese Patent Application No. 2016-054859 filed Mar. 18, 2016, the disclosures of all of which are hereby incorporated by reference in their entities.

TECHNICAL FIELD

The present invention relates to an optical interference tomographic image generating apparatus and a method of using the same.

BACKGROUND ART

Conventionally, an optical interference tomographic image generating apparatus for obtaining an image of a sample in a state in which a device held by a user abuts on the sample (see Patent Document 1), has been known.

In the technology disclosed by Patent Document 1, one of various supporting members, which is attachable to and detachable from a tip of a probe, is replaceably mounted on the tip of the probe gripped by the user. For example, a supporting member having a mirror is mounted on the tip of the probe, so that it is possible to irradiate a masticating surface of a molar with a measuring beam from the probe via the supporting member inserted into a mouth of a patient and the mirror.

PRIOR ART DOCUMENTS

Patent Document

PATENT DOCUMENT 1: JP 2014-61089

SUMMARY OF INVENTION

Problem to be Solved by Invention

The inventor had proposed optical interference tomographic image generating apparatuses capable of obtaining clear images of sampled in a stable state in which a user grips a probe. However, there was a room for further improvement. For example, it is possible to obtain an image of a masticating surface of the molar in a stable state provided by placing the supporting member attached to the probe on the masticating surface of the molar with influence of hand movement being decreased. However, it may be difficult to observe the image of the molar because an unnecessary image of the mirror enters the image of the molar.

In consideration of this situation, the present invention aims to provide an optical interference tomographic image generating apparatus and a method of using the same capable of obtaining an image with reduction of the influence of an unnecessary object near the sample.

Means for Solving Problem

To solve the problem, the inventor performed an experiment to obtain images in the optical interference tomographic image generating apparatus, while a reference position on a sample side is successively changed in which the mirror is disposed near the sample. In this experiment, a reference mirror on a reference optical path is disposed so as to equalize an optical path length of the reference optical path to an optical path length of a sample optical path in which a predetermined position on the side of the sample is defined as a reference position. As a result, it was found that there is a close relation between a phenomenon that an image of a mirror enters the image of the sample and a position of the reference mirror on the reference optical path.

An aspect of the present invention provides an optical interference tomographic image generating apparatus including: a device that is disposed on a sample optical path and brought abutting on the sample when a predetermined region of a tomographic plane of the sample is photographed as an object; a reference mirror disposed on a reference optical path, and an optical unit that splits a beam emitted by a light source into a beam directed to the reference mirror and a beam directed to the sample via the device and detects interference light between scattered light from the sample and a reflected beam returned from the reference mirror, the optical interference tomographic image generating apparatus generating an optical interference tomographic image from a detection signal of the interference light obtained time series, comprising:

a control device that performs image processing of vertically inverting an image generated from the detection signal in setting where the reference mirror is disposed so as to equalize the optical path length of the reference optical path to the optical path length of the sample optical path in which the reference point is set at a position deeper than the object along an optical axis of the sample.

An aspect of the present invention provides a method of using the optical interference tomographic image generating apparatus, comprising the step of:

disposing the reference mirror so as to equalize the optical path length of the reference optical path to the optical path length of the sample optical path in which the reference position is set to a position deeper than the object along an optical axis of the sample to reduce a ghost image of an unnecessary object arranged short of the sample along the optical axis.

According to the configuration, the optical interference tomographic image generating apparatus can obtain the image with influence by an unnecessary object being reduced, though the unnecessary object is disposed near the sample, because the apparatus can set the reference position on the sample side when the optical path length of the sample side and the optical path length of the reference optical path are equalized, to the position deeper than the object along an optical axis of the sample. Further, it is possible to obtain the image easy to observe it because the apparatus can set the reference position on the sample side when the optical path length of the sample side and the optical path length of the reference optical path are equalized, to the position deeper than the object and vertically invert the obtained upside-down image by the control device.

Further, in the optical interference tomographic image generating apparatus, it is preferable that the device comprises: a probe connected to the optical unit with an optical fiber; and a supporting body attachable to a tip end of the probe, wherein the supporting body includes a diagonal mirror for converting an optical axis into an optical axis having an orthogonal direction.

Accordingly, for example, the optical interference tomographic image when a masticating surface of a molar is irradiated with a beam can be obtained with the influence by the mirror being reduced.

It is preferable that in the optical interference tomographic image generating apparatus, the supporting member is configured to be attachable and detachable and the optical interference tomographic image generating apparatus further includes optical path length setting means capable of switchably setting the reference position on the side of the sample when the optical path length of the sample optical path and the optical length of the reference optical path are equalized between a position deeper than the object and a position short of the sample, along the optical axis of the sample.

Accordingly, when the supporting body including the diagonal mirror is attached, an image of the molar, etc. can be obtained with influence of the mirror being reduced by switching the reference position to the position deeper than the object. Further, when a supporting body having no mirror is attached in place of the supporting body including the diagonal mirror, it is possible to obtain the optical interference tomographic image when, for example, a front tooth is irradiated with a beam on the front surface.

Advantageous Effect of Invention

According to the present invention, there are provided the optical interference tomographic image generating apparatus and a using method capable of obtaining the image with the influence of the unnecessary object near the sample being reduced.

BRIEF DESCRIPTION OF DRAWINGS

FIGS. 2A, 2B, and 2C show a probe in which FIG. 2A is a side view showing a main part of the probe; FIG. 2B is an enlarged perspective view of a supporting member at a tip of the probe; and FIG. 2C is an enlarged view in an enlarge center longitudinal cross section of the supporting member.

FIGS. 3A, 3B, and 3C are drawings illustrating a reference position on the sample side so as to equalize the optical path length of the sample optical path to the optical path length of the reference light optical path, in which FIG. 3A shows a part of the sample optical path; FIG. 3B shows a part of the reference light path in which the reference position is set short of the sample; and FIG. 3C shows a part of the reference light path in which the reference position is set to a deeper position of the object.

FIGS. 4A, 4B, and 4C show illustrative views of the optical length setting means in FIG. 1 in which FIG. 4A shows a part of the sample optical path; FIG. 4B shows an optical path setting means when the reference position is set short of the sample; FIG. 4C shows an optical setting means when the reference position is set to a position deeper than the object.

FIGS. 10A to 10D show schematic views of a detection signal of interference beam, arrangement of the reference mirror, and images in which FIG. 10A and FIG. 10B show schematic views in a case that the reference position on the sample side is set short of the sample and FIG. 10C and FIG. 10D show schematic views in a case that the reference position on the sample side is at a position deeper than the object.

MODES FOR CARRYING OUT INVENTION

Figure 1:
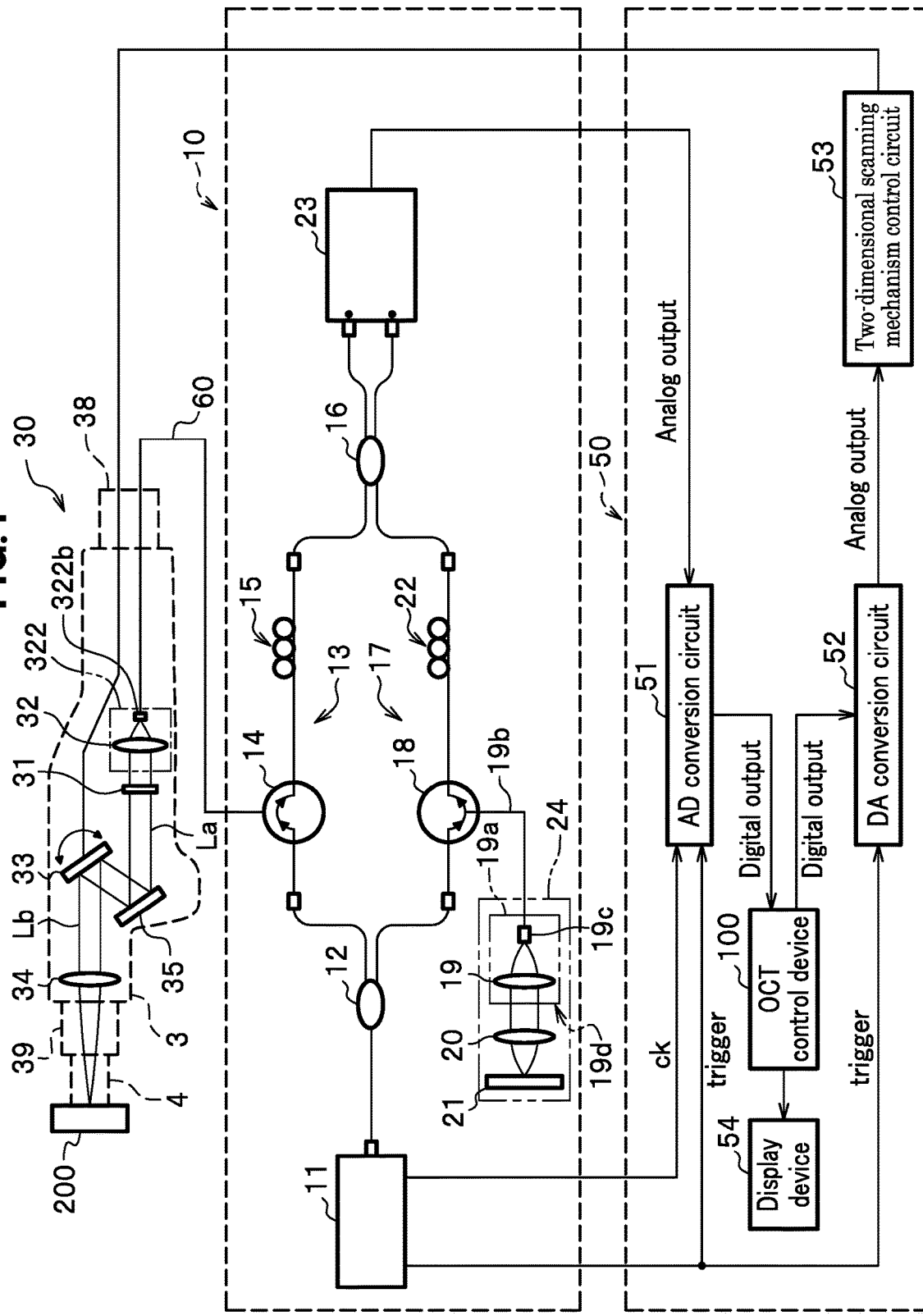
FIG. 1 is a block diagram schematically showing an optical interference tomographic image generating apparatus according to embodiments of the present invention.

An embodiment of an optical interference tomographic image generating apparatus according to the present invention is described below in detail with reference to drawings. It is noted that sizes of components, positional relations, etc. shown in the drawings may have exaggeration to make the explanation clearer.

As shown in FIG. 1, an optical interference tomographic image generating apparatus 1 mainly includes an optical unit 10, a probe 30, and a controller 50 and generates an optical interference tomographic image from a detection signal of interference light obtained time series. The probe 30 has premise that the probe 30 is disposed on a sample optical path and abutted on a sample 200 when a predetermined region on a tomographic plane of the sample 200 is photographed as an object.

Out of all regions of the topographical planes of the sample 200 in a depth direction along an optical axis, the predetermined region on the topographical plane of the sample 200 is a desired portion of observation target portion near an outer surface. When the sample 200 is, for example, a tooth, a region of topographical plane of a tooth crown is generally called an object. Dentists desire observation of topographical plane of the tooth crown mainly because it is difficult to observe a tooth root using a measuring light for visualizing an image at a depth of about 5 mm. In the drawings, as an object, a tooth crown portion of a molar is generally shown.

The optical unit 10 includes a light source, an optical system, and a detector, to which general various optical coherent tomographic systems can be applied. As shown in FIG. 1, the optical unit 10 includes a light source 11 periodically irradiates the sample 200 with a laser beam, a detector 23 detecting an internal information of the sample 200, optical fibers and various optical components, etc disposed on the optical path between the light source 11 and the detector 23. As the light source 11, a laser output device of, for example, SS-OCT (Swept Source Optical Coherence Tomography) system is usable. The sample 200 is, for example, a tooth.

General configuration of the optical unit 10 is described below.

A beam emitted by the light source 11 is split into a measuring beam and a reference beam by a coupler 12 as an optical split means. The measuring beam is directed to the sample 200 via the probe 30, and the optical path of the measuring beam is called sample optical path. The reference beam is directed to a reference mirror 21, and the optical path for the reference beam is called a reference optical path.

Out of them, the measuring beam is incident to the probe 30 from a circulator 14 of a sampling arm 13. When a shutter 31 of the probe 30 is in an open state, the measuring beam is converged on the measurement object 200 by a condenser lens 34 via a collimator 322, the two-dimensional scanning mechanism 33. The beam is scattered and reflected on the focused point and then scattered light and reflected light enters the condenser lens 34 again and returns to the circulator 14 via a two-dimensional scanning mechanism 33 and the collimator lens 322. The returned measuring beam is inputted into the detector 23 via a coupler 16.

On the other hand, the reference beam split by the coupler 12 is converged by a condenser lens 20 on the reference mirror 21 via a circulator 18 of a reference arm 17 and a collimator 19d and reflected at the converged point, transmits through the condenser lens 20 and the collimator 19d again, and returns to the circulator 18. The returned reference beam is inputted into the detector 23 via the coupler 16.

More specifically, the coupler 16 combines the measuring beam scattered and reflected at the measurement object 200 and the reference beam reflected by the reference mirror 21. The interference beam (interference light) as a result of combining is detected by the detector 23 as internal information. Further, a polarization controller 15 in a sampling arm 13 and a polarization controller 22 in a reference arm 17 are installed to return a polarized state of light generated in the optical coherence tomographic image generation apparatus 1 including the probe 30 to a less polarized state.

In the reference optical path, the collimator 19d includes a collimator lens 19, a lens holder 19a having a substantially hollow cylindrical shape housing the collimator lens 19 therein, and an optical fiber 19b of which one end is connected to a connector 19c and of which the other end is connected to a circulator 18.

In the reference optical path, an optical path length setting means 24 shifts a collimator 19d in an optical axis direction to change an optical path length from the coupler 12 to the reference mirror 21. A method of shifting the collimator 19d may be a manual method or an electric-powered method.

The optical path length setting means 24 may be provided using a configuration described in, for example, JP2012-217752 A. When this configuration is adopted, the optical path length setting means 24 is configured including, in addition to a condenser lens 20 and the reference mirror 21, for example, though not shown, a rail extending along the optical axis and a supporting member supporting the condenser lens 20 and the reference mirror 21 on the rail and a holding member holding the collimator 19d and being capable of advancing and retracting by a manual or electric-powered method.

The optical path length setting means 24 sets the reference position on the sample side for equalizing the optical path length of the sample optical path to the optical path length of the reference optical path length switchable to a position deeper than the object and a position short of the sample 200 along the optical axis of the sample 200. Hereinafter, when a reference position is simply referred, this means the reference position on the sample side for equalizing the two optical path lengths. Further, regarding the optical path length of the predetermined section, both-way optical path length is used. For example, out of the reference optical path, the reference beam goes and returns on the optical path of the optical fiber 19b connecting the circulator 18 and the connector 19c and the optical path from the connector 19c to the reference mirror 21. Accordingly, both ways of optical path is considered as the optical path lengths of these sections.

Further, out of the sample optical paths, the measuring beam goes and returns on the optical path by an optical fiber 60 connecting the circulator 14 and a connector 322b and an optical path from the connector 322b to the reference position the side of the sample 200. Accordingly, the both ways of the optical paths of these sections is considered as these sections.

The probe 30 introduces the laser beam from the optical unit 10 into the sample 200 and introduces the reflected light into the optical unit 10. The probe 30 is a device which is disposed in the sample optical path and abutted on the sample 200.

The probe 30 includes, for example, a main body 3, a first tube 38 installed on a base end side, a second tube 39 installed on a tip end side of the main body 3, and a supporting body 4 fitted into the second tube 39.

Main Body

Figure 2A:
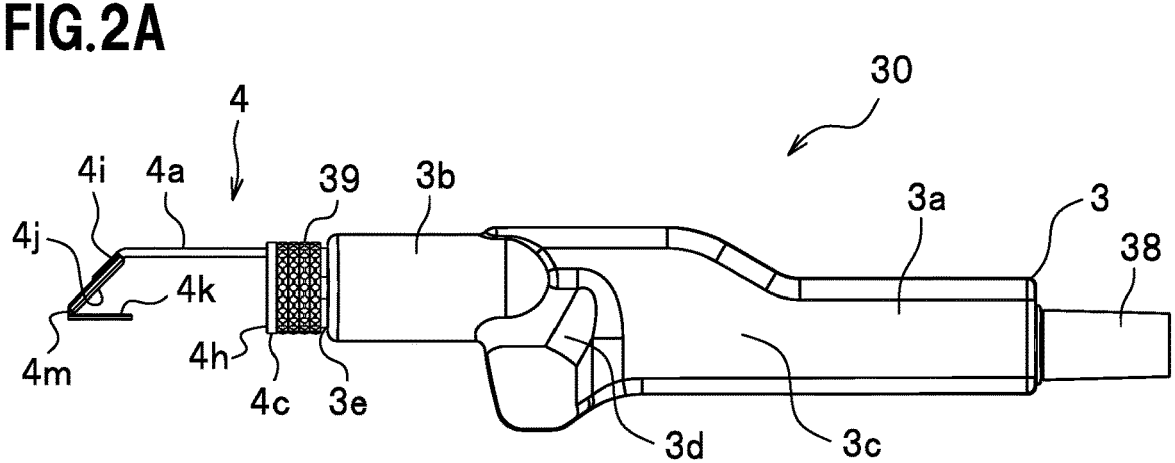

The main body 3 includes, as shown in FIG. 2A, a base end section 3a, a tip end section 3b, a collimator lens housing section 3c disposed between the base end section 3a and the tip end section 3b, and a scanning mechanism housing section 3d.

The base end section 3a is formed in a substantially rectangular tube of which corners are beveled, and the first tube 38 is fitted thereto.

The tip end section 3b is formed in a substantially circular tube shape and houses the condenser lens 34 (see FIG. 1). The tip end section 3b supports the second tube 39 at an opening 3e thereof.

The collimator lens housing section 3c is formed on a tip side of the base end section 3a. The collimator lens housing section 3c is a section housing the collimator lens 32 (see FIG. 1) thereinside and formed to have an inner diameter greater than that of the base end section 3a. The collimator lens housing section 3c is formed to have a diameter slantwise enlarged portion on an upper side thereof and the lower side is horizontally formed.

The scanning mechanism housing section 3d is formed on a tip side thereof of the collimator lens housing section 3c. The scanning mechanism housing section 3d is formed thicker to have an outer diameter greater than that of the base end section 3a and the tip end section 3b. The scanning mechanism housing section 3d houses the two-dimensional scanning mechanism 33 (see FIG. 1) at a portion formed expanding upwardly. The scanning mechanism housing section 3d houses a mirror 35 at a portion expanding downwardly.

The main body 3 is formed in a straight shape in a side view as shown in FIG. 2A. Accordingly, the main body 3 has a shape easy to hold and operate because the scanning mechanism housing section 3d and the collimator lens housing section 3c can be held such that a person grips a pencil. Though not shown, at a predetermined position of the main body 3, a plurality of operation buttons are provided. The operation buttons includes, for example, a button for bringing the shutter 31 of the probe 30 in an open state and a button for starting measurement (photographing).

As shown in FIG. 1, installed in the main body 3 are a collimator 322, the two-dimensional scanning mechanism 33, the condenser lens 34, the mirror 35 are fixed mainly to a frame body (not shown).

The collimator 322 includes the collimator lens 32, the connector 322b mounted on a holder holding the collimator lens 32, and the optical fiber 60 of which one end is connected to the connector 322b and the other end is connected to the circulator 14.

The two-dimensional scanning mechanism 33 reflects a beam incident from one of sides of the mirror 35 and the condenser lens 34 toward the other side while a position is shifted by time-division driving. In the embodiment, the two-dimensional scanning mechanism 33 is configured with two galvanometer mirrors of which rotational axes are orthogonal with each other and drive motors for respective galvanometer mirrors, etc.

The condenser lens 34 is a lens converges beam (measuring beam) reflected by the galvanometer mirrors of the two-dimensional scanning mechanism 33 and irradiates the object with the beam.

The mirror 35 reflects the beam (measuring beam) incident from the side of the collimator lens 32 toward the side of the two-dimensional scanning mechanism 33. The beam from the mirror 35 is reflected by one of the galvanometer mirrors and incident to the condenser lens 34 via the other one of the galvanometer mirror. Accordingly, the mirror 35 is fixed to a predetermined portion of the scanning mechanism housing section 3d in such a state that the mirror plane is inclined to the optical path of the measuring beam by 45 degrees. The mirror 35 is installed being inclined toward a side of the collimator lens 32 in the scanning mechanism housing section 3d.

The first tube 38 is a component having a substantially tube shape whose tip side is fitted into inside of the base end section 3a of the main body 3 and arranged in such a state that the base end thereof protrudes from the base end section 3a. The first tube 38 is a component supporting a communication cable connected to the controller 50, the optical fiber 60 connected to the optical unit 10, etc. which penetrate therethrough.

The first tube 38 and the base end section 3a are formed extending straight along an optical path La of the measuring beam introduced into the base end section 3a to the mirror 35.

The second tube 39 is a component supporting the supporting body 4 by the main body 3 and formed in a substantially circular tube shape. The second tube 39 is inserted into the opening 3e of the main body 3 and holds the supporting body 4 at the tip end section 3b of the main body 3 through a connecting member (not shown) attachable and detachable (replaceable) and rotatably. The second tube 39 and the tip end section 3b are formed extending straight along an optical path Lb of the measuring beam from the two-dimensional scanning mechanism 33 to the opening 3e. The optical path Lb is parallel to the optical path La. The measuring beam advances from the optical path La and is reflected by the mirror 35 and the two-dimensional scanning mechanism 33 and goes on the optical path Lb. On an outer circumferential surface of the second tube 39 regarding the axial direction thereof, roughness is formed therearound.

On photographing, the operator grips the probe 30 and brings the probe 30 abutting on the sample 200 to avoid hand movement shot, etc. For example, the supporting body 4 abuts on the sample 200.

The supporting body 4 mainly includes, as shown in FIG. 2A, an engaging member 4c attachably and detachably inserted into the main body 3 through the second tube 39, a rod 4a, a diagonal mirror 4j, and a fixing member 4k. The supporting body 4 is formed of a stainless steel, etc.

Figure 2B:
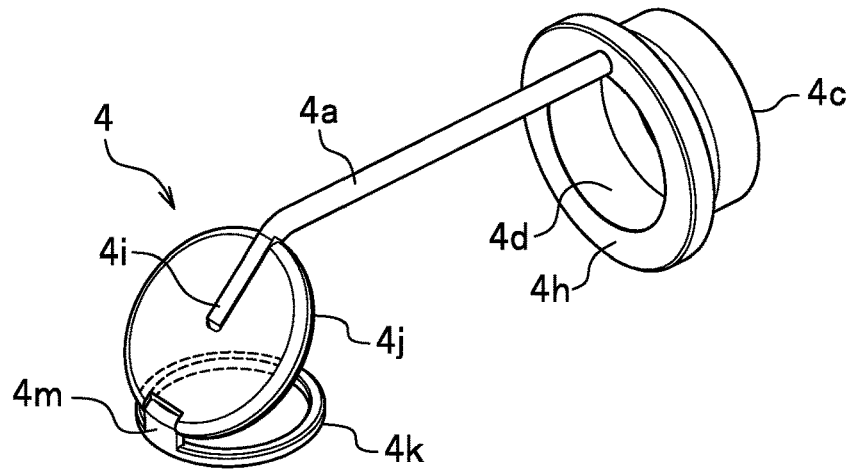

The engaging member 4c is arranged in front of the condenser lens 34 and has an opening 4d for irradiation of the sample 200 with the measuring beam and collecting scattered light as shown in FIG. 2B. A base end portion of the rod 4a is welded and fixed to the engaging member 4c on an upper front side of the flange portion 4h. The rod 4a includes a bent portion 4i of which tip is bent downwardly by about 45 degrees. The diagonal mirror 4j is connected to the bent portion 4i. The diagonal mirror 4j is a reflection mirror changing an optical axis of the condenser lens 34 to an orthogonal direction by 90 degrees.

The fixing member 4k is a component having a ring shape and abutted on the sample 200 to support the supporting body 4. The fixing member 4k is horizontally fixed to the diagonal mirror 4j diagonally arranged.

Figure 2C:
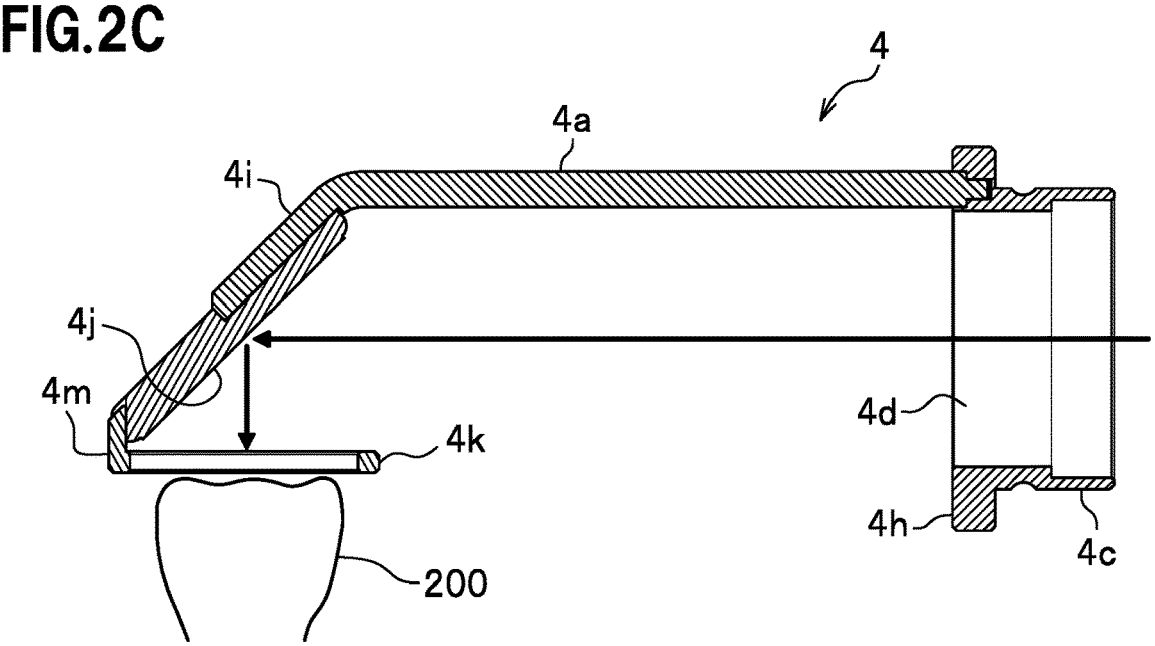

When photographing is made with the probe 30, abutment of the supporting body 4 connected to the main body 3 on the sample 200 as shown in FIG. 2C can provides support of the probe 30 in a stable state. The supporting body 4 can be kept always clean by replacement of a new one or a cleaned one.

Optical Coherence Tomography

As shown in FIG. 1, the controller 50 includes an A/D converting circuit 51, a D/A converting circuit 52, a two-dimensional scanning mechanism control circuit 53, a display device 54, and an OCT (Optical Coherence Tomography) control device 100.

The A/D converting circuit 51 is a circuit for converting an analog output signal of the detector 23 into a digital signal. In the embodiment, the A/D converting circuit 51 starts acquiring a signal synchronously with a trigger (trigger) outputted by the laser emitting device as the light source 11, acquires the analog output signal of the detector 23 in response to timing of a clock signal ck also outputted by the laser emitting device, and converts the analog output signal into the digital signal. The digital signal is inputted into the OCT control device 100.

The D/A converting circuit 52 is a circuit for converting the digital output signal of the OCT control device 100 into an analog signal. In the embodiment, the D/A converting circuit 52 converts the digital signal of the OCT control device 100 into the analog signal synchronously with the trigger (trigger) outputted by the light source 11. The analog signal is inputted into the two-dimensional scanning mechanism control circuit 53.

The two-dimensional scanning mechanism control circuit 53 is a driver for controlling the two-dimensional scanning mechanism 33 in the probe 30. The two-dimensional scanning mechanism control circuit 53 outputs motor drive signals for controlling between driving and stopping the motors of the galvanometer mirrors or the galvanometer mirror synchronously with an output cycle of the laser beam emitted by the light source 11 on the basis of the analog output signal of the OCT control device 100.

The two-dimensional scanning mechanism control circuit 53 performs a process of changing the angle of the mirror surface by rotating a rotation shaft of one of the galvanometer mirrors and a process of changing the angle of the mirror surface by rotating the rotation shaft of the other of the galvanometer mirrors at different timings.

The display device 54 is a device for displaying an optical coherent tomographic image (hereinafter may be simply referred to as a topographical image) generated by the OCT control device 100. The display device 54 comprises, for example, a liquid crystal display (LCD: Liquid Crystal Display), etc.

The OCT control device 100 performs measurement by controlling the two-dimensional scanning mechanism 33 synchronously with the beam emitted by the light source 11 as well as performs control for generating the OCT image, etc of the measuring object 200 from data obtained by converting the detection signal of the detector 23. The OCT image, etc. can be generated by a known method of generating optical coherence tomographic image, etc. In addition, the tomographic image, etc. may be generated by the method disclosed in, for example, JP2012-211797 A.

The OCT control device 100 comprises a computer including, for example, a CPU (Central Processing Unit) or GPU (Graphics Processing Unit), a RAM (Random Access Memory), a ROM (Read Only Memory), a hard disk drive, and an input/output interface.

An OCT control device 100 performs an image process to vertically invert the image generated from the detection signal when the reference mirror on the reference optical path is disposed so as to equalize an optical path length of the reference optical path to an optical path length of an optical path of a sample optical path with reference to a predetermined position on the sample side which is deeper than the position of the sample along the optical axis of the sample.

Next, the reference position on the side of the sample when the optical path length of the sample optical path and the optical path length of the reference optical path are equalized is described below referring to FIGS. 3A to 3C.

Figure 3A:
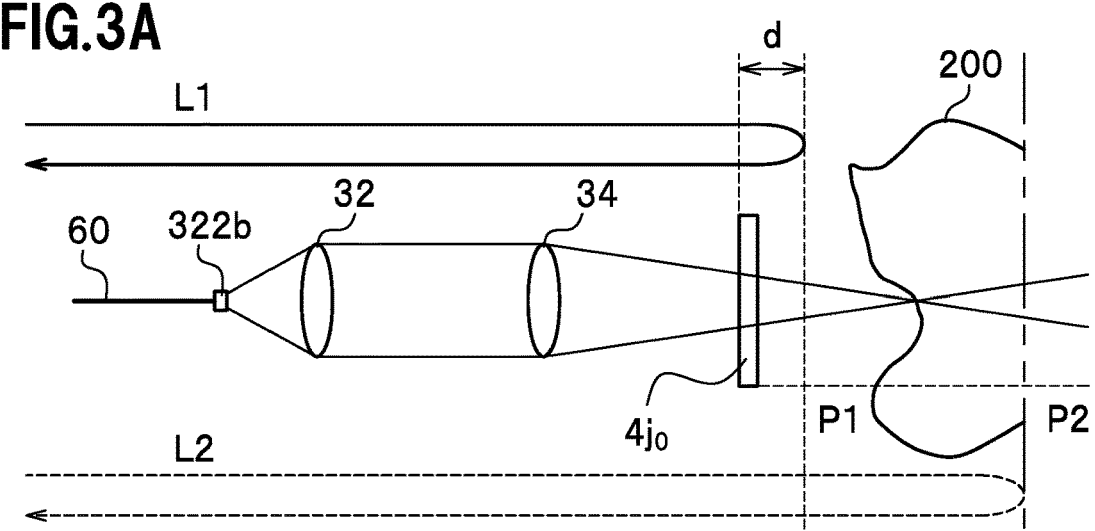

FIG. 3A shows a part of the sample optical path.

More specially, FIG. 3A schematically shows the optical fiber 60, the connector 322*b*, the collimator lens 32 and the condenser lens 34 arranged in the probe 30 (see FIG. 1). Further, FIGS. 3A to 3C schematically show a situation that a diagonal mirror 4*j*0 of the supporting body 4 (see FIGS. 2A to 2C) attached to the probe 30 is arranged near the sample 200. The sample 200 is a molar and shown in which a masticating surface thereof is directed to the left in FIG. 3A. P1 and P2 represent reference positions on the side of the sample, respectively. Out of the reference positions, the reference position P1 indicated with a broken line near the masticating surface shows an example of the reference position in a case that the reference position P1 is set short of the sample 200. The reference position P2 indicated with a two-dot chain line at a border between a tooth crown and a tooth root of the molar shows an example of the reference position in a case that the reference position P1 is set to a position deeper than the object along the optical axis of the sample 200.

Figure 3B:
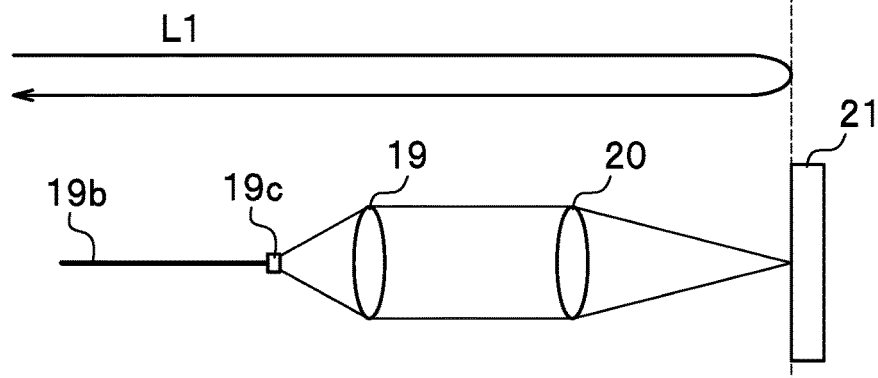
Figure 3C:
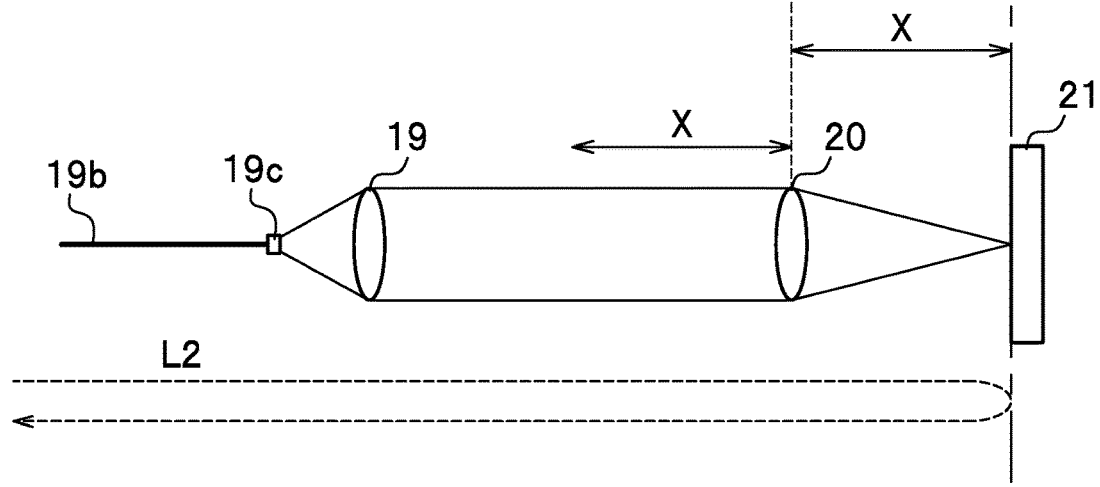

FIG. 3B and FIG. 3C show a part of the reference optical path. More specially, FIG. 3B and FIG. 3C are schematic illustrations of arrangements of the optical fiber 19*b*, the connector 19*c*, the collimator lens 19, the condenser lens 20, and the reference mirror 21 which are arranged on the reference optical path. In FIG. 3C, the condenser lens 20 and the reference mirror 21 are shifted by a distance X to a deeper side along the optical axis relative to FIG. 3B. The distance X is equal to a distance from the reference position P1 shown in FIG. 3A to the reference position P2.

FIG. 3B shows a part of the reference optical path when the reference position P1 is set to the reference position P1 which is shorter of the sample 200. As shown, the reference mirror 21 is disposed so as to equalize the optical path length L1 on the reference optical path shown in FIG. 3B to an optical path length L1 of the sample optical path via the reference position P1 on the side of the sample shown in FIG. 3A. In the measurement of the optical coherence tomographic image, generally, the reference position on the sample side to equalize the optical path length on the sample optical path to the optical path length of the reference optical path is set short of the sample.

FIG. 3C shows a part of the reference optical path when the reference position is set to the reference position P2 which is at a position deeper than the object. As shown, the reference mirror 21 is disposed so as to equalize the optical path length L2 on the reference optical path shown in FIG. 3C to an optical path length L2 of the sample optical path via the reference position P2 on the side of the sample shown in FIG. 3A.

The diagonal mirror 4*j*0 shown in FIG. 3A represents a diagonal mirror bottom portion nearest the sample 200 in a region (for example, a rectangular region) to which the measuring beam is applied in FIG. 2C. However, the diagonal mirror 4*j*0 is simply called the diagonal mirror 4*j*0. In this example, the diagonal mirror 4*j*0 is disposed remote from the reference position P1 short of the sample by a distance d.

There is another method of setting by switching between the reference position P1 and the reference position P2 other than the method of shifting the positions of the condenser lens 20 and the reference mirror 21 as described referring to FIG. 3B and FIG. 3C. Instead, it can be provided to move the position of the collimator lens 19 on the reference optical path. In this case, switching of reference positions is described referring to FIGS. 4A to 4C.

Figure 4A:
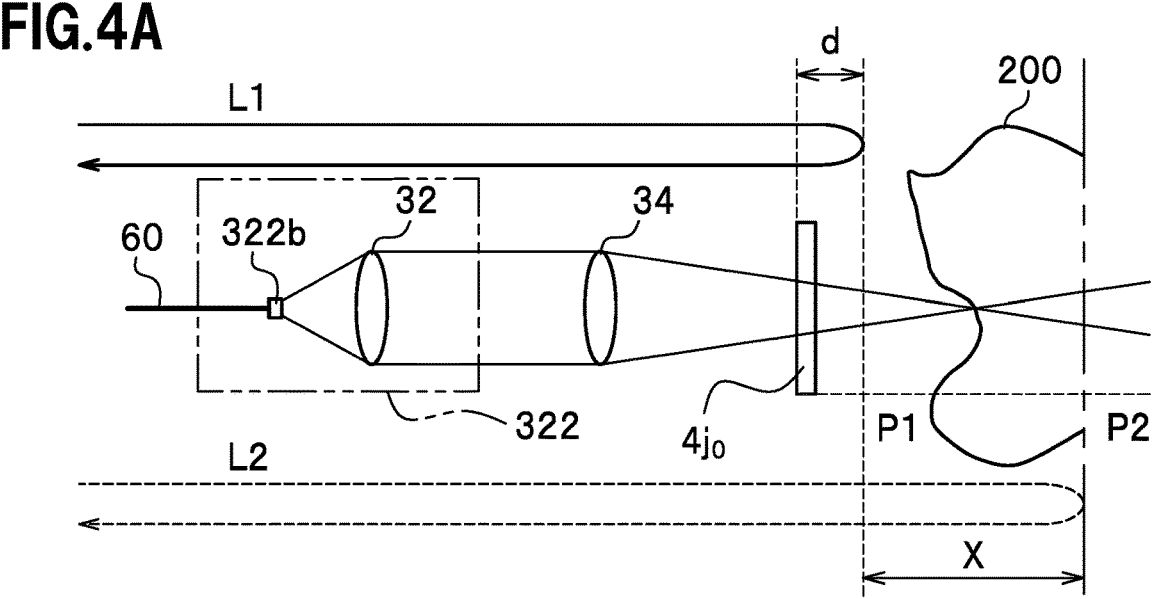

FIG. 4A is different from FIG. 3A in that the collimator 322 including the optical fiber 60, the connector 322*b*, and the collimator lens 32 is added.

Figure 4B:
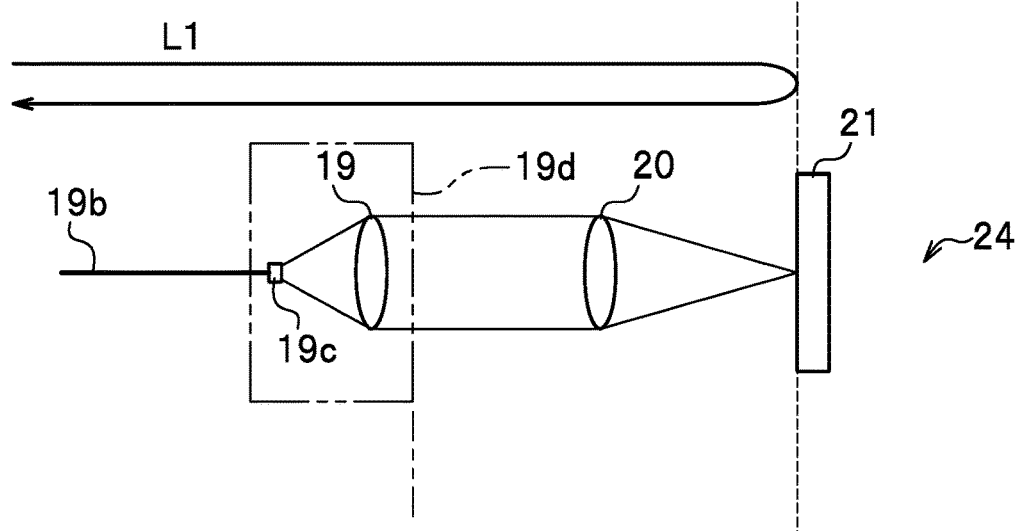

FIG. 4B schematically shows the optical path length setting means 24 shifting in an optical axis direction the collimator 19*d* including an optical fiber 19*b*, a connector 19*c*, and the collimator lens 19. The lens holder 19*a* of the collimator 19*d* is not shown.

In FIG. 4B, it is premised that, in the optical path length setting means 24, along a rail on the supporting member, the collimator 19*d* is brought close to the condenser lens 20 and the reference mirror 21 which are fixed on a supporting member (not shown). FIG. 4B schematically showing a state that the optical path length L1 of the reference optical path is equal to the optical path length L1 of the sample optical path shown in FIG. 4A under premise of bring the collimator 19*d* closer. In other words, shifting the collimator 19*d* on the reference optical path and fixing the collimator 19*d* at the current position shown in FIG. 4B is equivalent to that the reference position on the sample side when the optical path length of the sample optical path and the optical length of the sample optical path are equalized is set to the reference position P1 which is short of the sample 200.

Figure 4C:
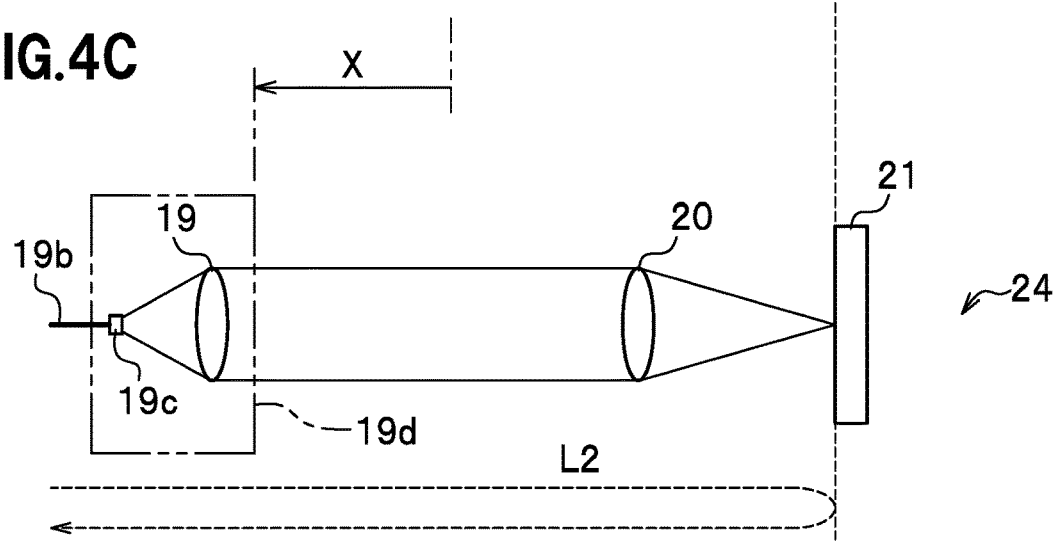

In FIG. 4C, it is premised that, in the optical path length setting means 24, the collimator 19*d* is brought remote from the condenser lens 20 and the reference mirror 21 fixed to the supporting member along the rails on a supporting member (not shown). FIG. 4C schematically shows a state that the optical path length L2 of the sample side is equal to the optical path length L2 of the sample side shown in FIG. 4A under the premise that the collimator 19*d* is brought remote. In other words, shifting the collimator 19*d* on the sample optical path and fixing the collimator 19*d* at the current position shown in FIG. 4C is equivalent to that the reference position on the sample side when the optical length of the sample optical path and the optical path length of the reference optical path are equalized, is set to the reference position P2 which is deeper than the object. In FIG. 4C, the position of the collimator 19*d* is shifted on a short side of the sample by the distance X along the optical axis relative to FIG. 4B.

[Advantageous Effect of Setting the Reference Position on the Sample Side to a Position Deeper than the Object]

Next, an advantageous effect of setting the reference position on the sample side to a position deeper than the object is described below.

The inventor of the present application performed an experiment after preparing an optical interference tomographic image generation apparatus in which the reference position on the sample side when the optical length of the sample optical path and the optical length of the reference optical path are equalized can be changed. In this experiment, the mirror is disposed near the sample, and the OCT images, etc. respectively displayed were observed while the reference position on the sample side is successively changed. Generally, in the measurement of the OCT images in the department of ophthalmology, the reference position on the sample side when the two optical lengths are equalized is set short of the observing target part of the eye (sample).

On the other hand, in dentistry, because it is desired to observe, for example, a masticating surface or the OCT images when the masticating surface of a molar is irradiated with the beam as a front view, the mirror for applying the beam to the masticating surface of the molar becomes necessary. This is not applied to the use in ophthalmology, but a specific situation inherent to the dentistry. For example, to observe the molar, it is supposed that a fixing device and a mirror are disposed at tip of the device, and the device is inserted into an oral cavity of a patient, and the image is obtained in such a stable state that the fixing device is fixed on the masticating surface of the molar.

Accordingly, in the optical interference tomographic image generating apparatus prepared for the above-described experiment, first, the reference position on the sample side for equalizing the optical length on the sample optical path and the optical path length of the reference optical path, is set short of the sample (molar) as performed in the general method. In this condition, as shown in FIG. 2C, the fixing member 4k of the supporting body 4 is fixed on the masticating surface of the sample (molar) 200, and an image of the molar (a stereoscopic image, a front image, and an OCT image) is obtained.

Specific examples of the obtained images are described, referring to FIG. 5 to FIG. 8.

Figure 5:
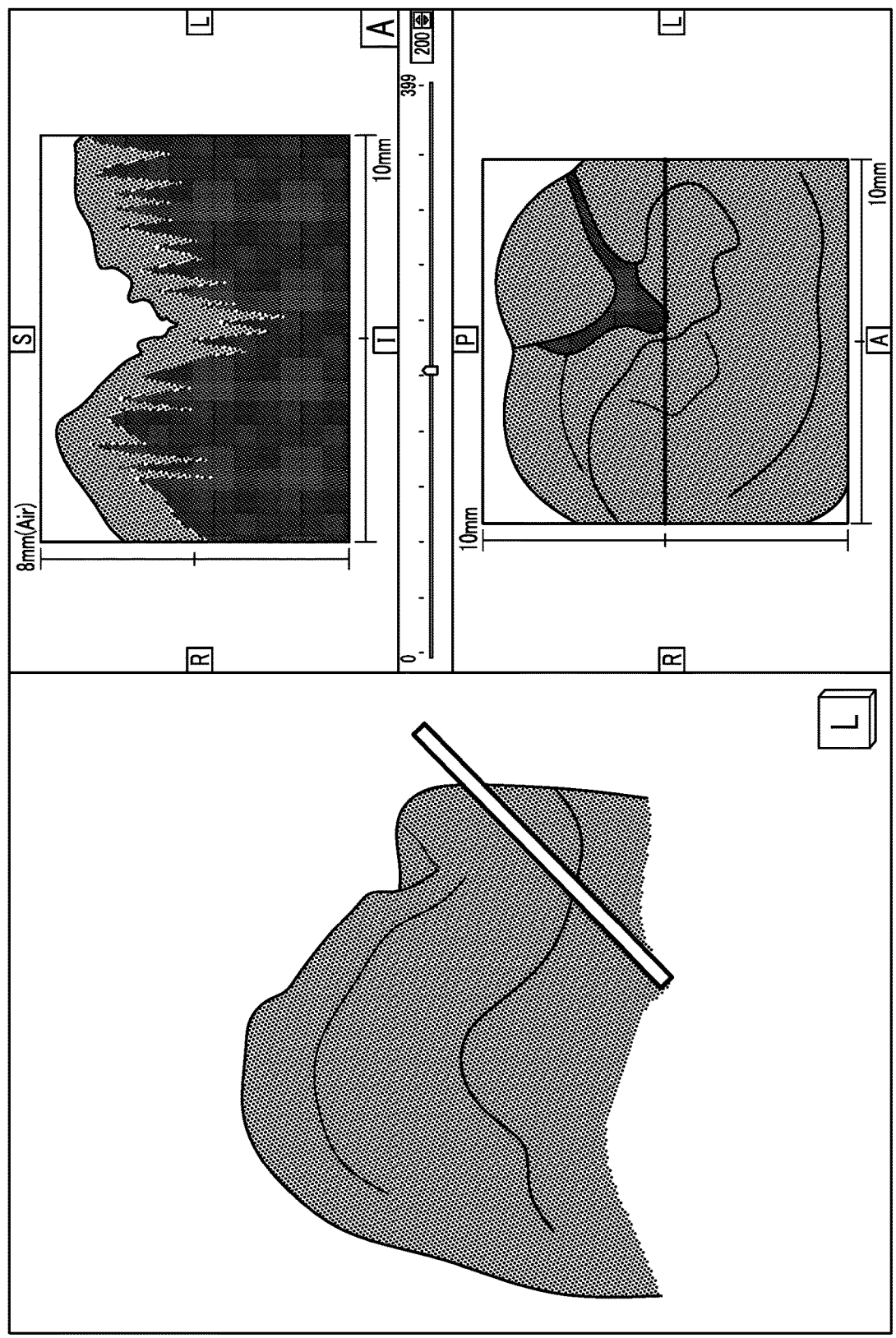
FIG. 5 shows schematic views of images obtained in a state that the reference position is set short of the sample.
Figure 6:
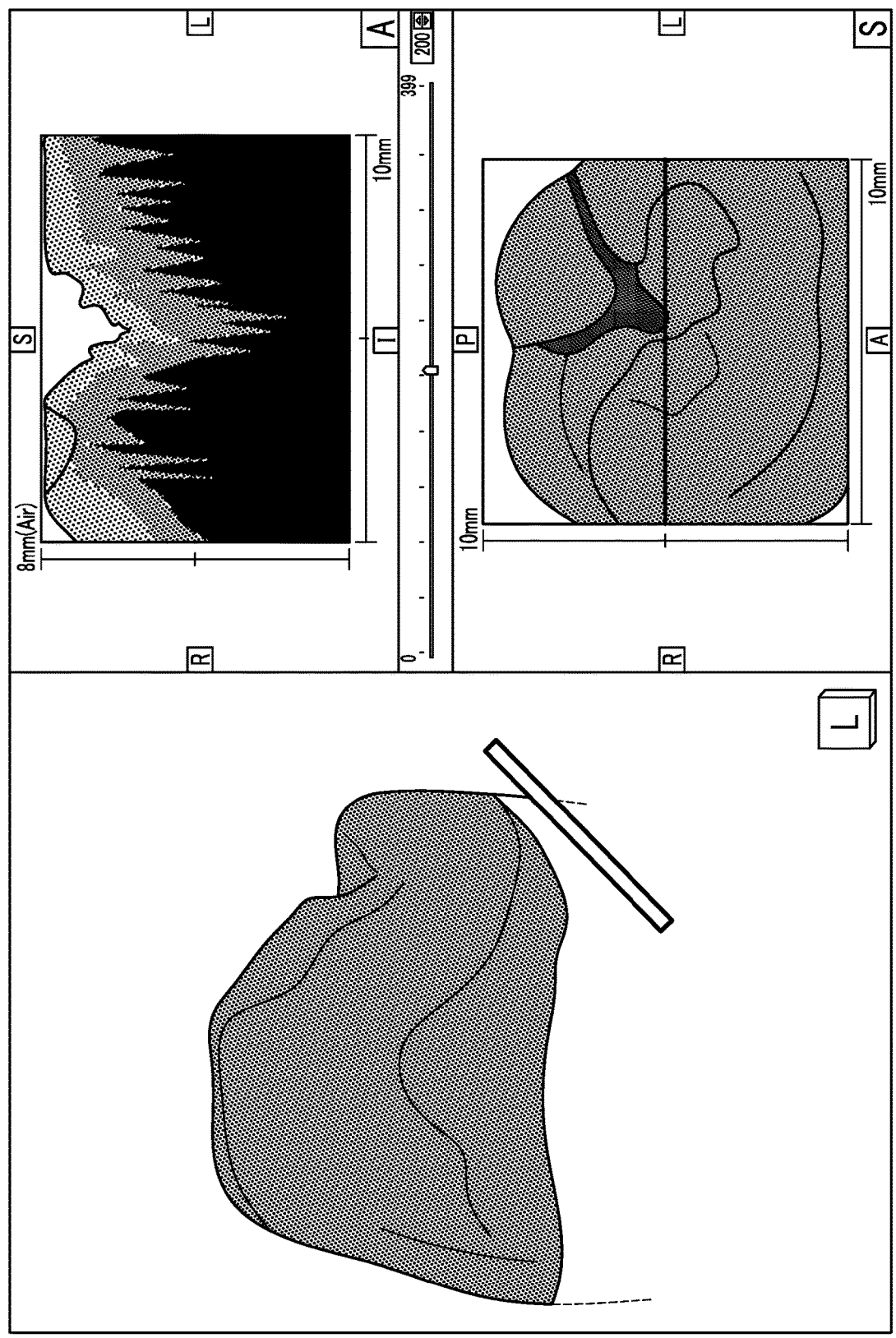
FIG. 6 shows schematic views of images obtained in a state in which the reference position is shifted to a deeper position from the position in the state of FIG. 5.
Figure 7:
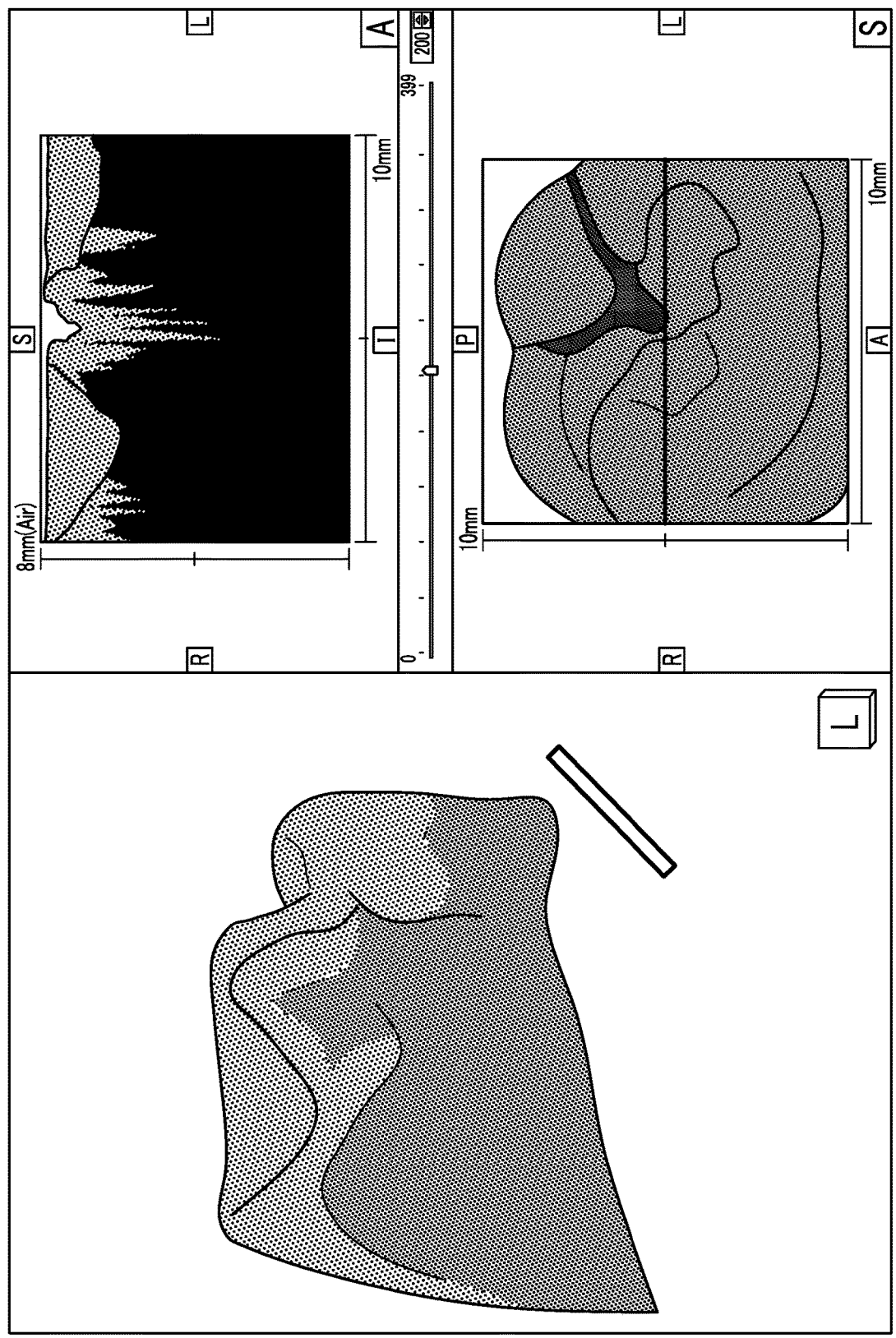
FIG. 7 shows schematic views of images obtained in a state in which the reference position is shifted to a deeper position from the position in the state of FIG. 6.
Figure 8:
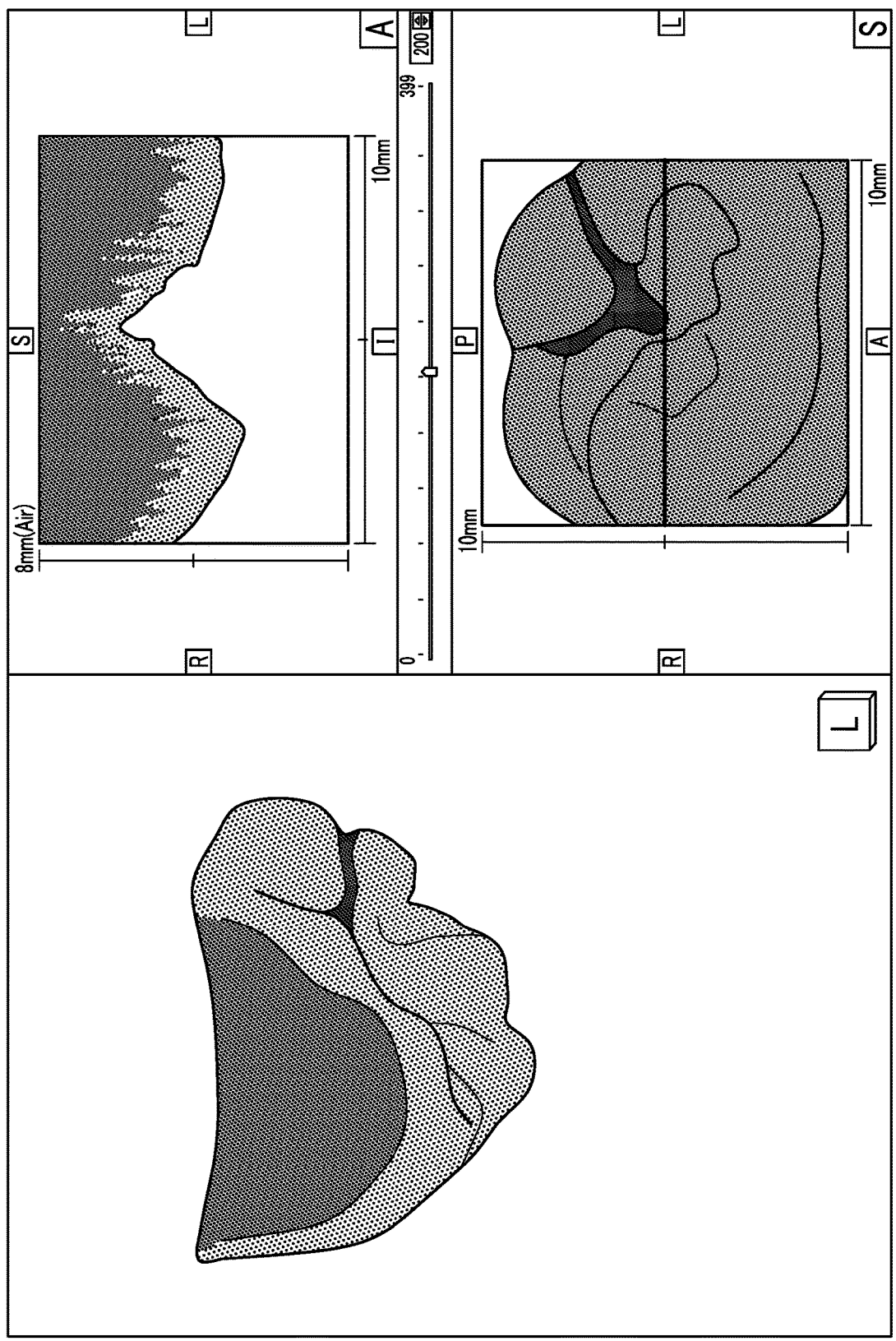
FIG. 8 shows schematic views of images obtained in a state in which the reference position is shifted to a deeper position from the position in the state of FIG. 7.

FIG. 5 shows schematic illustrations of a stereoscopic image arranged on a left side thereof, a front image arranged on the lower-right thereof, and an OCT image arranged on the upper-right thereof. Incidentally, a front view, a rear view, a left side view, a right side view, upper and lower surfaces are called an S surface, an I surface, an L surface, an R surface, a P surface, and an A surface, respectively. FIGS. 6 to 8 are different from FIG. 5 in that the reference positions on the sample side when the images are generated, have been changed.

For example, the stereoscopic image shown in FIG. 5 is an image of the molar in a view indicated by a cube at a right corner of the image, i.e., an image of the molar in view of L-surface side.

Further, the front image shown in FIG. 5 is a two-dimensional image obtained by sum total of data in a depth direction of the S surface (front surface) in the stereoscopic image. The front image indicates internal information which originally cannot be seen on an outmost surface of the S surface.

The OCT image shown in FIG. 5 is an image on a tomographic plane which is in parallel to the A surface (lower surface) and taken along a lateral line arranged at a substantially center of the front view image. For example, four hundreds of the OCT images are obtained corresponding to four hundreds of cross sections. A desired image can be displayed by specifying one of them.

As shown in the stereoscopic image shown in FIG. 5, it is confirmed that on the image of the molar, an image of the mirror is displayed. After that, an experiment has been performed to display an image of the molar generated while the reference position on the sample side when the optical path length of the sample optical path and the optical path length of the reference optical path are equalized, is gradually changed along the optical axis of the sample to a deeper position. As a result, as shown in FIGS. 6 and 7, on the displayed image, the image of the mirror becomes indistinct while the image gradually shifts downward and becomes small and indistinct. On the other hand, the image of the molar gradually shift upward and folded-over image are shown from upper edges of the images. Finally, as shown in FIG. 8, the image of the molar is displayed upside-down while the image of the mirror is almost no image of the mirror.

As a result, the inventor found out that there is a close relation between the phenomenon that a ghost image of an unnecessary object near the sample is displayed together with the necessary sample image and the position of the reference mirror 21 (see FIG. 1) on the reference optical path. This is described below, referring to FIGS. 10A to 10D.

Figure 10A:
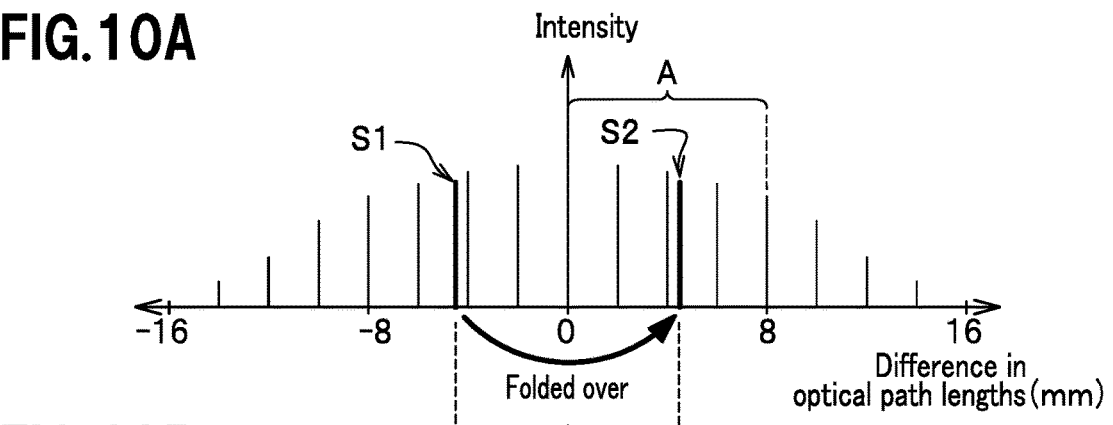

FIG. 10A is a graphic charts schematically showing an example of a detection signal of the interference beam obtained when the image of the mirror is taken together with the image of the sample under a condition that the diagonal mirror is disposed near the sample, and the reference position on the sample side is set short of the sample and is fixed. An axis of abscissa of the chart represents a half of a difference obtained by subtracting the optical path length of the reference optical path from the optical path length of the sample optical path as a distance difference (mm) of the optical path lengths. The reason why the distance difference is represented as a half of the distance difference is that the optical length is shown in consideration of two ways, but the distance reflected on the photographed image is a half of the distance. The distance difference varies in accordance with a position where a signal is detected on the sample side under a condition that the reference position is fixed on the sample sides. In FIG. 10A, an origin of the charts represents the reference position on the sample side when the optical path length of the sample optical path and the reference optical path are equalized. The origin corresponds to the reference position P1 (see FIG. 4A) which is set short of the sample. An axis of ordinate of the chart represents an intensity of the signal (power, dB).

As shown in FIG. 10A, at a position where the distance difference of the optical path length is zero, the intensity of the signal is highest because the optical length of the reference optical path is equal to the optical path length of the sample optical path. An intensity of the signal detected at such a position on the sample side that the distance difference between the optical path length of the sample optical path and the optical path length of the reference measurement beam becomes larger, more decreases. Further, the intensity of the signal is left-right symmetrical on a border at the origin.

Figure 10B:
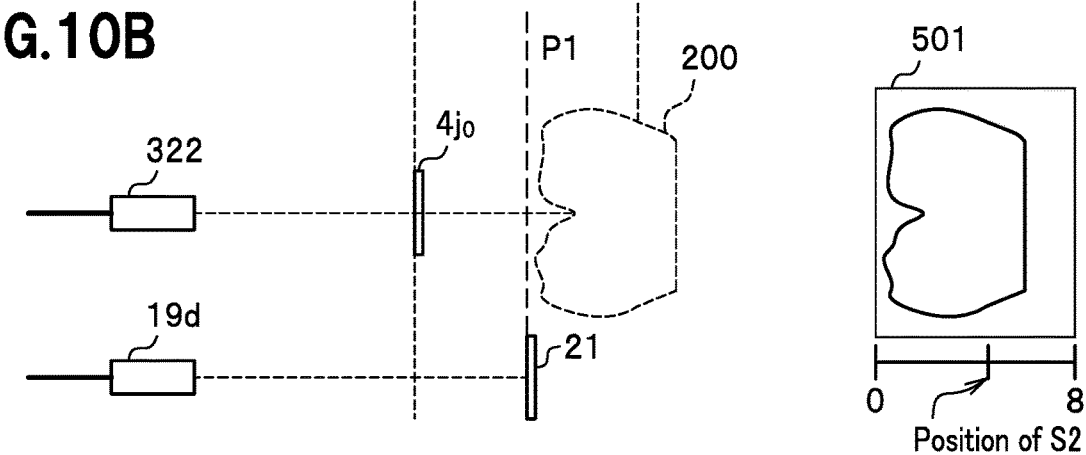

FIG. 10B is a drawing simply showing a combination of a part of the sample optical path (see FIG. 4A) and a part of the optical path length setting means 24 (see FIG. 4B) on the reference optical path and schematically shows it in which the diagonal mirror 4j0 and the reference mirror 21 are with association with an axis of abscissa (distance difference) of FIG. 10A.

The reference mirror 21 on the reference optical path is arranged with association with the origin of the graphical chart of FIG. 10A. The sample 200 on the sample optical path is arranged at a position slightly shifted from the origin in a plus direction (right). The diagonal mirror 4j0 on the sample optical path is arranged at a position slightly shifted in a minus direction (left).

A signal S1 shown on the graphical chart of FIG. 10A is caused by an influence of the diagonal mirror 4j0. The signal S1 caused by the influence of the diagonal mirror 4j0 is shown at a position of which distance difference of the optical path length is "−4.5 mm". This corresponds to that the distance d (see FIG. 4A) from the reference position P1 on the sample side to the diagonal mirror 4j0 is 4.5 mm. Because the signal S2 is generated by the signal S1 being folded over on the graphical chart, it is considered that an OCT image 501 obtained as shown in FIG. 10B includes an unnecessary signal of the mirror at the position of the signal S2.

On the graphical chart of FIG. 10A, the signal S2 is folded over within a region of a photographing possible distance A. The value of the photographing possible distance A is a constant related with a value (mm) of distance shown on the axis of abscissa. As shown in the graphical chart, in a region where the distance difference of the optical path length exceeds the value of the photographing possible distance A, the intensity of the signal is rapidly attenuated. The value of the photographing possible distance A is, for example, 8 mm. The photographing possible distance A is determined by a distance in a depth direction of the topographical image determined by a coherence length of the beam emitted by the light source 11 (see FIG. 1) and a sampling rate of the interference beam.

The coherence length corresponds to a distance where a power spectrum attenuates by 6 dB which is related to a performance of the light source 11 (see FIG. 1).

A sampling rate of the interference beam means a frequency of a sampling clock signal for sampling the interference signal detected by the detector 23 (see FIG. 1) to generate an OCT image, etc. of the sample 200 in the OCT control device 100 (see FIG. 1).

Figure 10C:
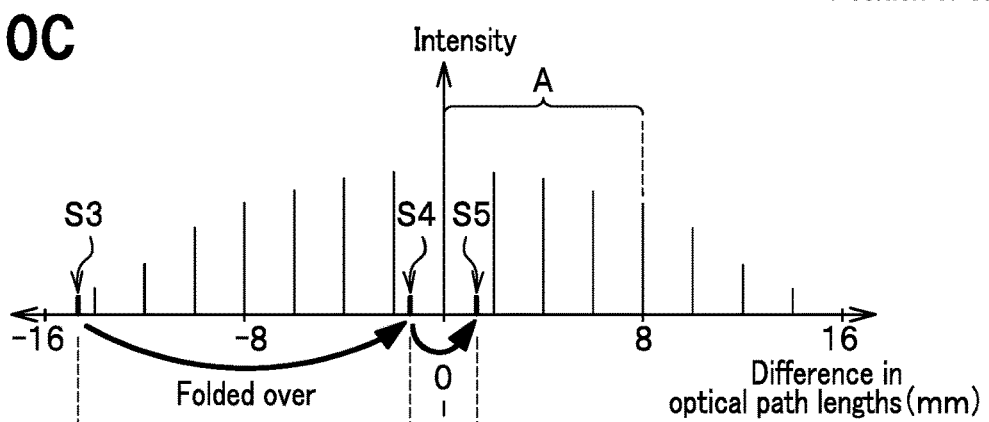

FIG. 10C is a graphic chart schematically showing an example of the detection signal of the interference beam obtained when the influence of the image of the mirror is reduced under a condition that the diagonal mirror is disposed near the sample, and the reference position on the sample side is set to a position deeper than the object and is fixed. A method of observing the graphical chart of FIG. 10C is the same as that of FIG. 10A. However, in the graphical chart of FIG. 10C, the origin corresponds to the reference position P2 (see FIG. 4C) which is set to the position deeper than the object.

Figure 10D:
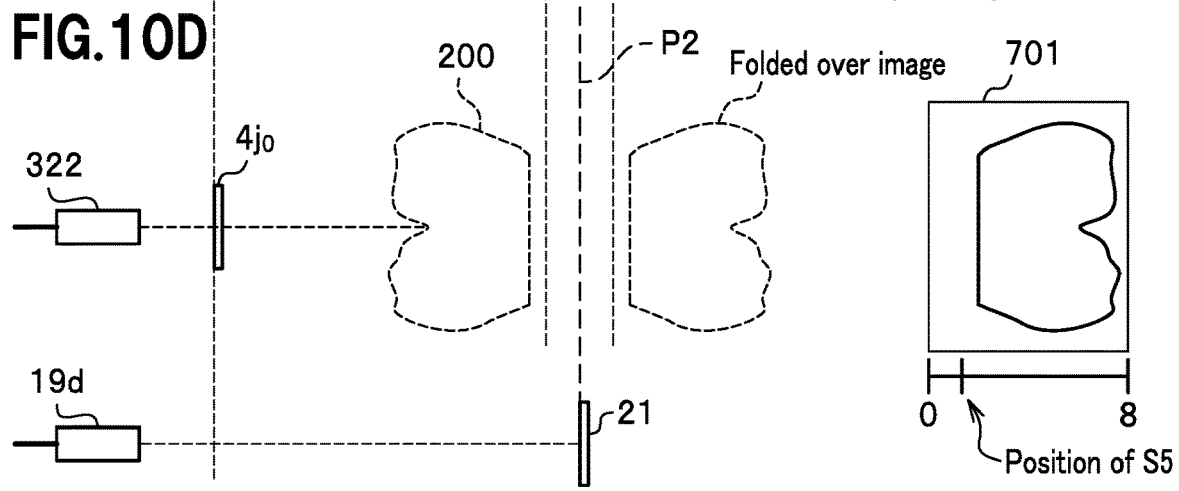

FIG. 10D is a drawing simply showing a combination of a part of the sample optical path (see FIG. 4A) and a part of the optical path length setting means 24 (see FIG. 4C) on the reference optical path and schematically shows the diagonal mirror 4j0 and the reference mirror 21 with association with an axis of abscissa (distance difference) of FIG. 10C.

The reference mirror 21 on the reference optical path is arranged with association with the origin of the graphical chart of FIG. 10C. The sample 200 on the sample optical path is arranged at a position slightly shifted from the origin in a minus direction (right). The diagonal mirror 4j0 on the sample optical path is arranged at a position slightly shifted in a minus direction (left).

A signal S3 shown on the graphical chart of FIG. 10C is caused by an influence of the diagonal mirror 4j0. The signal S3 caused by the influence of the diagonal mirror 4j0 is shown at a position of which distance difference of the optical path length is around "−14.6 mm". This corresponds to that the distance (see FIG. 4A) from the reference position P2 on the sample side to the diagonal mirror 4j0 is "14.6 mm".

The distance from the reference position P2 to the diagonal mirror 4j0 is, as shown in FIG. 4A, a sum value of the distance X from the reference position P2 to the reference position P1 and the distance d from the reference position P1 to the diagonal mirror 4j0. For example, when the distance from the reference position P2 to the diagonal mirror 4j0 is 14.6 mm and the distance d is 4.5 mm, the distance X from the reference position P2 to the reference position P1 corresponds to 10.1 mm which is a difference between these distances. The distance X is longer than a photographing possible distance A and shorter than twice photographing possible distance A.

When these relational equations are satisfied, it is easy to determine arrangement of the reference mirror 21 or the collimator lens 19 on the reference optical path. In other words, when the reference position P1 is known, it is enough to determine the position remote from the reference position P1 by a distance longer than the photographing possible distance A and shorter than twice of the photographing possible distance A as a reference position P2. Accordingly, it is possible to reduce the influence of the unnecessary object and obtain a clear image by weakening the interference signal of the unnecessary object such as the diagonal mirror, etc. near the sample with the intensity of the interference signal of the sample being kept.

The reason why an intensity of a signal S3 by the diagonal mirror 4j0 shown on the graphical chart of FIG. 10C is lower than an intensity of the signal S1 by the diagonal mirror 4j0 shown on the graphical chart of FIG. 10A, is that a distance from the origin of the graphical chart in FIG. 10A to a position of the signal S3 (for example, 14.6 mm) is greater than the distance (for example, 4.5 mm) from the origin of the graphical chart of FIG. 10A to the signal S1.

As shown in FIG. 10C, in the detection signal of the interference beam, a signal is folded over at a position as a center of which distance difference of the optical path between the sample optical path and the reference optical path is zero, and a signal is folded over at a position as a center remote from the origin by the photographing possible distance A. When the photographing possible distance A is 8 mm, the signal S3 by the diagonal mirror 4j0 is folded over at the position as a center of which distance difference of the optical lengths is "−8 mm", so that a signal S4 is generated. Further, the signal S4 is folded over at the origin as a center, so that a signal S5 is generated.

Figure 9:
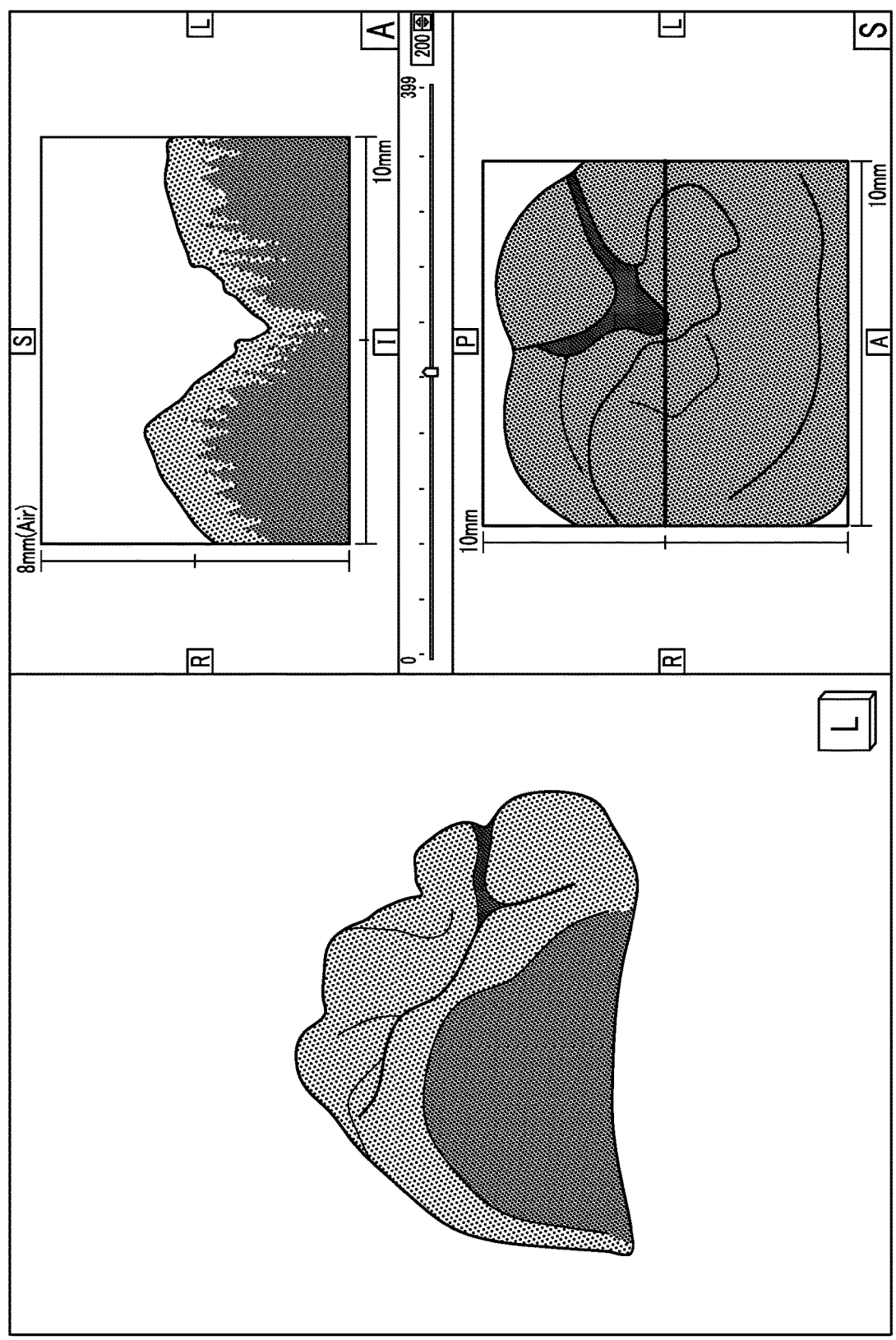
FIG. 9 shows schematic views of images vertically inverted of a left side image and tomographic images of FIG. 8.

On the graphical chart of FIG. 10C, the signal S5 is folded within a range of the photographing possible distance A. Accordingly, as shown in FIG. 10D, it is supposed that an unnecessary signal of the mirror may enter an OCT image 701. However, in this example, the position of the signal S5 on the OCT image 701 is outside the region where the tooth crown is clearly photographed. In addition, an intensity of the signal S3 representing the diagonal mirror 4j0 is originally small, so that the diagonal mirror is almost invisible. On the other hand, an upside down image is obtained as the OCT image 701, but as shown in FIG. 9, the image easy to observe can be obtained by vertically inverting in the image processing by the OCT control device 100. Further, FIG. 9 is different from FIG. 8 in that the stereoscopic image arranged on the left side and the OCT image arranged upper-right are vertically inverted, respectively.

Next, a method of using the optical interference tomographic image generating apparatus 1 is described below, occasionally referring to FIGS. 1, 2A to 2C, 4A to 4C, and 11. An operator turns a power switch (not shown) on and sets the reference position on the sample side to a position deeper than the object (the reference position P2 in FIG. 4A) when the optical length of the sample optical path and the optical length of the reference optical path are equalized by electromotion or manual operation in advance. The operator operates a button for bringing the shutter 31 shown in FIG. 1 to an open state and a button for starting measurement (photographing).

When the sample 200 is, for example, a molar, the operator inserts the supporting body 4 connected to the tip portion of the probe 30 gripped by the operator into an oral cavity of the patient from the front of the patient, brings the supporting body 4 abutting on the molar (the sample 200) for positioning on the patient, and starts measurement. The OCT control device 100 performs image processing of vertically inverting the obtained image and displays the processed image on a display device 54.

Figure 11:
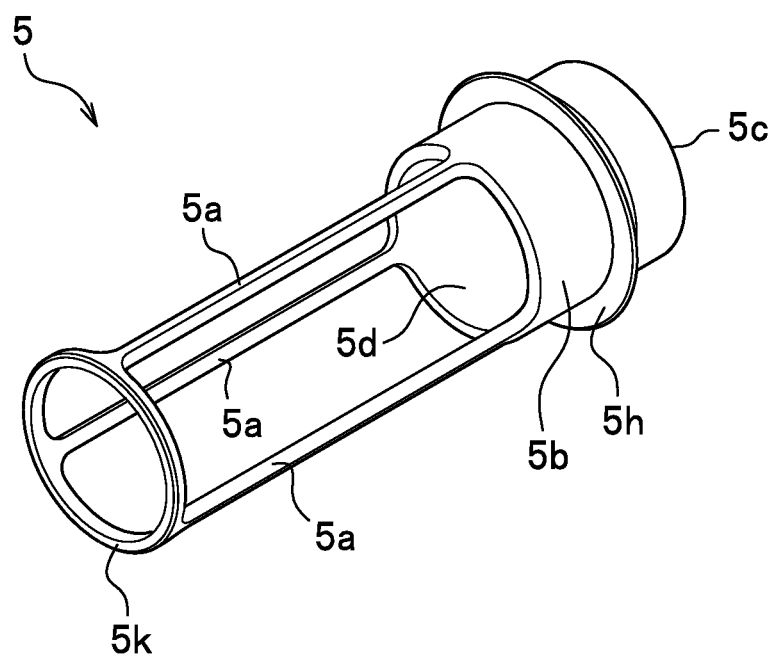
FIG. 11 is a perspective view of a structural example of the supporting member.

On the other hand, when the sample 200 is, for example, a front tooth, the operator attaches, for example, a supporting body 5 only for the front tooth, having no mirror as shown in FIG. 11 to the probe 30. The supporting body 5 includes a member generally formed in a substantially circular tube shape. More specifically, the supporting body 5 is integrally formed of an engageable tube member 5c, having an opening 5d, to be connected to the second tube 39 (see FIG. 2A), a flange portion 5h in front of and continuous with the engageable tube member 5c, a tube portion 5b in front of and continuous with the flange portion 5h, three shaft portions 5a in front of and continuous with the tube portion 5b, and a fixing portion 5k formed in front of the shaft portions 5a and having a ring shape. The optical path length of the supporting body 5 is equal to the optical path length of the supporting body 4 shown in FIG. 2B. The optical path length of the supporting body 5 is a length from a right end of the engageable tube member 5c to a left end of the fixing portion 5k in FIG. 11. The optical path length of the supporting body 4 is a sum of a length from a right end of the engaging member 4c to the diagonal mirror 4j and a length from the diagonal mirror 4j to a lower end of the fixing member 4k as shown by arrows in FIG. 2C. In this case, the operator performs positioning on the patient by bringing the fixing portion 5k of the supporting body 5 of the probe 30 abutting on a front of the front tooth (the sample 200) and then similarly performs the measurement.

As described above, the optical interference tomographic image generating apparatus 1 can obtain an image easy to observe the image because the apparatus can set the reference position on the sample side when the optical path length of the sample optical path and the optical path length of the reference are equalized, to a position deeper than the object and vertically invert the obtained image, though an unnecessary object is arranged near the sample.

The optical interference tomographic image generating apparatus according to embodiments of the present invention has been described above, but is not limited to the embodiments. For example, the apparatus includes the optical path length setting means 24 for changing the optical path length of the reference optical path. Instead, the apparatus may include an optical path length setting means for changing the optical path length of the sample optical path by a similar mechanism. However, in this case, it is necessary to replace the condenser lens 34 itself to change the focal length of the condenser lens 34 between when the reference position on the sample side to a position deeper than the object and the focal length of the condenser lens 34 and when the reference position is set to a position short of the sample. Accordingly, it is preferable to make setting on the side of reference optical path to easily change the reference position on the sample side.

The optical interference tomographic image generating apparatus may have a configuration capable of switching between a first operation mode and a second operation mode in the optical path length setting means 24, the first operation mode providing a measurement of which reference position on the side of the sample is set to a position deeper than the object, the second operation mode providing a measuring of which reference position on the side of the sample is set to a position short of the sample 200. In this case, the OCT control device 100 performs only the first operation mode in which the image processing for vertical inversion, but does not perform the second operation mode.

The optical interference tomographic image generating apparatus may be confirmed as a special apparatus in which the mirror is disposed near the sample. In this case, it is enough that the reference position on the sample side is previously set to a position deeper than the object and fixed. Further, the supporting body 4, which is separated from the probe 30, includes the diagonal mirror 4j. However, it is also allowed to use a special probe including a diagonal mirror and a fixing device.

The supporting body 4 attached to the probe 30 is used for photographing the sample 200 as the molar in which the masticating surface of the molar is irradiated with a beam, it is suitable for photographing not only the masticating surface but also a lingual side and a Buccal aspect. The supporting body 4 is suitable for photographing not only the molar but also, for example, photographing tissues in the oral cavity, an OCT image on a side of a front tooth one the lingual side, etc.

The example using the galvanometer mirror has been described. However, the invention is not limited to this and the invention may use a two-dimensional MEMS mirror. An element of the two-dimensional MEMS mirror element is formed to have a three-layer configuration including a silicon layer in which a mirror for total reflection and a movable member such as a flat coil, etc. for electromagnetically driving through generation of an electromagnetic force, a ceramic pedestal, and a permanent magnet. The two-dimensional MEMS mirror element can be controlled in static or dynamic inclination in an X-axis direction and a Y-axis direction in accordance with a magnitude of a current allowed to flow through a coil.

In the present invention, the sample is not limited to tooth. Further, the present invention can be also applied to medical devices other than the dentistry, nondestructive inspection, etc.

DESCRIPTION OF REFERENCE SYMBOLS 1 optical interference tomographic image generating apparatus
4, 5 supporting body
4j, 4j0 diagonal mirror
10 optical unit
11 light source
21 reference mirror
24 optical path length setting means
30 probe
100 OCT control device
200 sample

The invention claimed is:

1. An optical interference tomographic image generating apparatus comprising:

a device that is disposed on a sample optical path and brought abutting on a sample when a predetermined region of a tomographic plane of the sample is photographed as an object at a reference position;

a reference mirror disposed on a reference optical path;

an optical unit including an optical coupler configured to split a beam emitted by a light source into a beam directed to the reference mirror and a beam directed to the sample via the device and detects interference light between scattered light from the sample and a reflected beam returned from the reference mirror, the optical interference tomographic image generating apparatus generating an optical interference tomographic image from a detection signal of the interference light obtained in time series;

wherein a reference optical length from the optical coupler to the reference mirror is equalized to a sample optical length of the sample optical path from the optical coupler to the reference position deeper than the sample to reduce a ghost image of an unnecessary object; and a control device that performs image processing of vertical inverting an image generated from the detection signal, when the reference position is deeper than the sample along an optical axis of the sample.

2. The optical interference tomographic image generating apparatus as claimed in claim 1, wherein the device comprises:

a probe connected to the optical unit with an optical fiber; and a supporting body attached to a tip end of the probe, wherein the supporting body includes a diagonal mirror for converting an optical axis into an optical axis having an orthogonal direction; and wherein an image of the diagonal mirror is generated over the optical interference tomographic image as the ghost image of the unnecessary object.

3. The optical interference tomographic image generating apparatus as claimed in claim 2, wherein the supporting body is configured to be attachable to and detachable from the tip end of the probe, the apparatus further comprising optical path length setting means capable of switchably setting the reference position on the side of the sample between a position deeper than the sample and a position short of the sample, along the optical axis of the sample.

* * * * *